US006960696B1

(12) United States Patent
Davis

(10) Patent No.: US 6,960,696 B1
(45) Date of Patent: Nov. 1, 2005

(54) 2,4-DINITROPHENOL AND ENVIRONMENTALLY FRIENDLY METHODS FOR MAKING THE SAME

(75) Inventor: Matthew C. Davis, Ridgecrest, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 94 days.

(21) Appl. No.: 10/911,764

(22) Filed: Jul. 29, 2004

(51) Int. Cl.$^7$ .......................................... C07C 205/00
(52) U.S. Cl. ..................................... 568/711
(58) Field of Search ....................... 568/711

(56) References Cited

U.S. PATENT DOCUMENTS 3,933,926 A * 1/1976 Salter et al. ............... 568/710
4,540,832 A * 9/1985 Arndt et al. ................ 568/711
5,946,638 A 8/1999 Jayasuriya et al.
5,977,418 A 11/1999 Damavarapu et al.

OTHER PUBLICATIONS

Hill, H.B., Torrey, J. Jr., "CXV. On Nitromalonic Aldehyde" *Amer Chem J.* 22, 89-110 (1899).

* cited by examiner

*Primary Examiner*—Michael L. Shippen
(74) *Attorney, Agent, or Firm*—Charlene A. Haley

(57) ABSTRACT

An environmentally friendly methods for making 2,4-dinitrophenyl compound comprising, providing a nitromalondialdehyde, providing a nitroacetone, reacting the nitromalondialdehydes with the nitroacetone to produce a mixture, and subjecting the mixture to a cyclodehydrative mechanism to produce environmentally friendly 2,4-dinitrophenyl compound. Embodiments of the present invention include the 2,4-dinitrophenyl compound produced by the methods of described above.

4 Claims, No Drawings

2,4-DINITROPHENOL AND ENVIRONMENTALLY FRIENDLY METHODS FOR MAKING THE SAME

The invention described herein may be manufactured and used by or for the government of the United States of America for governmental purposes without the payment of any royalties thereon or therefor.

FIELD OF THE INVENTION

The present invention relates to environmentally friendly methods for making 2,4-dinitrophenyl, and more specifically, utilizing cyclodehydrative condensation mechanism for making the 2,4-dinitrophenyl that does not produce unwanted highly toxic nitration isomers.

BACKGROUND OF THE INVENTION

Current methods of synthesizing trinitrotoluene (TNT) involve successive mixed-acid nitrations of the petrochemical toluene (Milligan, B., "Isomer Distribution in Mixed-Acid Nitration of Toluene. Evidence for Mass-Transfer Effects on Selectivity" *Ind Eng Chem Fundam,* 25(4), 783–789 (1986). During this process, some undesired nitration isomers occur ($\alpha$-, $\beta$-, and $\gamma$-trinitrotoluene) as well as incomplete nitration products (2,4- and 2,6-dinitrotoluene). These unwanted isomers are removed by sellite (sodium sulfite) washings. Isomers with nitro groups ortho to one another react with the sulfite generating ionic, water-soluble products. These washes have a characteristic red color, hence the name 'red water'. These washings are highly toxic and very expensive to destroy (incinerate). Because of this 'red water' problem, there are no North American plants that will produce TNT. Currently, all U.S. needs for TNT are supplied from overseas sources where environmental standards are mild or non-existent.

A report by Hill and Torrey explain the chemistry and analogous condensation of nitromalondialdehyde (Hill, H. B., Torrey, J. Jr., "CXV. On Nitromalonic Aldehyde" *Amer Chem J.* 22, 89–110 (1899)). However, the report does not teach nor suggest the use of dinitro-compounds to make trinitro aromatics (TNT).

U.S. Pat. No. 5,946,638 issued on Aug. 31, 1999 to Jayasuriya, et al., and U.S. Pat. No. 5,977,418 issued on Nov. 2, 1999 are based on a process for regaining the nitration of toluene in the presence of zeolites. The products from the nitration process in these patents do not include trinitrotoluene (TNT) aromatics. Although the zeolites help to make the nitration reaction more regioselective, there still remain small percentages of unwanted isomers that must be removed (i.e. sellite washings) This present invention is completely different from the above patents, there is not nitration of an aromatic ring, hence no regioisomer issues. The invention described here is a novel ring forming reaction of two nitro components to form an aromatic ring in a completely regiospecific manner.

There exists a need in the art for an environmentally friendly alternative to the current manufacturing process for the high explosive 2,4,6-trinitrotoluene (TNT) which does not produce the highly toxic nitration isomers and products responsible for "red water" waste.

SUMMARY OF THE INVENTION

The present invention relates to environmentally friendly methods for making 2,4-dinitrophenyl compound comprising, providing a nitromalondialdehyde, providing a nitroacetone, reacting the nitromalondialdehydes with the nitroacetone to produce a mixture, and subjecting the mixture to a cyclodehydrative mechanism to produce environmentally friendly 2,4-dinitrophenyl compound. Embodiments of the present invention include the 2,4-dinitrophenyl compound produced by the methods of described above.

It is to be understood that the foregoing general description and the following detailed description are exemplary and explanatory only and are not to be viewed as being restrictive of the present invention, as claimed. Further advantages of this invention will be apparent after a review of the following detailed description of the disclosed embodiments and in the appended claims.

DETAILED DESCRIPTION OF THE INVENTION

The present invention relates to methods for making 2,4,6-trinitrotoluene (TNT) compounds, picric acid explosives, and 2,4-dinitrophenyl compounds by utilizing environmentally friendly cyclodehydrative condensation mechanisms.

Embodiments of the present invention include an environmentally friendly method for making 2,4,6-trinitrotoluene (TNT) compounds comprising, providing nitromalondialdehydes, providing dinitro-compounds, reacting the nitromalondialdehydes with the dinitro-compounds to produce aldol- intermediate compounds, and subjecting the intermediate compounds to a cyclodehydrative mechanism to produce 2,4,6-trinitrotoluene (TNT) compounds in an environmentally friendly manner. These embodiments of the present invention include the nitromalondialdehydes comprising about 26 to about 53 weight % and the dinitro-compounds comprising about 47 to about 74 weight %. In other embodiments, the dinitro-compounds comprises at least one of 1,3-dinitro-2-methyl-2-propanol or 1,3-dinitroacetone. According to the methods of the present 2,4,6-trinitrotoluene (TNT) compounds, the cyclodehydrative mechanism includes subjecting the intermediate compound to dehydration to remove excess $H_2O$.

Embodiments of the present invention include the 2,4,6-trinitrotoluene (TNT) compounds produced by the environmentally methods described above. Further embodiments of the present invention also include an environmentally friendly 2,4,6-trinitrotoluene (TNT) compound comprising about 26 to about 53 weight % of nitromalondialdehyde and about 47 to about 74 weight % of dinitro-compound, wherein reacting the nitromalondialdehyde with the dinitro-compound produces aldol- intermediate compounds, wherein the aldol- intermediate compounds are subjected to cyclohydrative mechanism to remove excess $H_2O$ to produce an isomer-free 2,4,6-trinitrotoluene (TNT) compound. The 2,4,6-trinitrotoluene (TNT) compound according to the present invention includes the dinitro-compound comprising at least one of 1,3-dinitro-2-methyl-2-propanol or 1,3-dinitroacetone.

Additional embodiments of the present invention includes an environmentally friendly method for making 2,4,6-trinitrotoluene (TNT) compounds comprising, providing nitromethylamino-hexafluorophosphates, providing dinitro-compounds, reacting the trimethinium hexafluorophosphates with the dinitro-compounds to produce aldol- intermediate compounds, and subjecting the intermediate compounds to a cyclodehydrative mechanism to produce environmentally friendly 2,4,6-trinitrotoluene (TNT) compounds.

According to embodiments of the present invention, the nitromethylamino-hexafluorophosphates includes 2-nitro-1,3-bis(dimethylamino)-trimethinium. In other embodiments, the dinitro-compounds comprises at least one of 1,3-dinitro-2-methyl-2-propanol or 1,3-dinitroacetone. In another embodiment, the nitromethylamino-hexafluorophosphates comprises about 75 to about 80 weight % and dinitro-compounds about 20 to about 25 weight %. Yet in other embodiments, the nitromethylamino-hexafluorophosphates comprises about 78 weight % and the dinitro-compounds about 22 weight %. The cyclodehydrative mechanism includes subjecting the intermediate compound to dehydration to remove excess $H_2O$ and $HNMe_2$. Embodiments of the present invention include the 2,4,6-trinitrotoluene (TNT) compounds produced by this environmentally friendly method.

Another embodiment of the present invention includes an environmentally friendly 2,4,6-trinitrotoluene (TNT) compound comprising about 75 to about 80 weight % of nitromethylamino-hexafluorophosphates and about 20 to about 25 weight % of dinitro-compound, wherein reacting the trimethinium hexafluorophosphates with the dinitro-compound produces aldol- intermediate compounds, wherein the aldol-intermediate compounds are subjected to cyclohydrative mechanism to remove excess $H_2O$ and $HNMe_2$ to produce an isomer-free 2,4,6-trinitrotoluene (TNT) compound.

Embodiments of this 2,4,6-trinitrotoluene (TNT) compound comprise about 78 weight % of nitromethylamino-hexafluorophosphates and about 22 weight % of dinitro-compound. In other embodiments, the nitromethylamino-hexafluorophosphates includes 2-nitro-1,3-bis(dimethylamino)-trimethinium. Other embodiments include dinitro-compound comprising at least one of 1,3-dinitro-2-methyl-2-propanol or 1,3-dinitroacetone.

Another embodiment includes the method for making environmentally friendly picric acid explosive comprising, providing a nitromalondialdehyde, providing a dinitroketone, reacting the nitromalondialdehydes with the dinitroketone to produce a mixture, and subjecting the mixture to a cyclodehydrative mechanism to produce environmentally friendly picric acid explosive. Embodiments of the present invention include the dinitroketone comprising about 55 to about 60 weight % and the nitromalondialdehyde comprising about 40 to about 45 weight %. In other embodiments, the dinitroketone comprisies about 56 weight % and the nitromalondialdehyde comprises about 44 weight %. Other embodiments include the dinitroketone comprising at least one of 1,3-dinitroacetone or nitroacetone. The method according to the present invention includes the cyclodehydrative mechanism subjecting the mixture to dehydration to remove excess $H_2O$.

Embodiments of the present invention include the picric acid explosive produced by this environmentally friendly method. Another embodiment includes an environmentally friendly picric acid explosive comprising about 40 to about 45 weight % of nitromalondialdehyde and about 55 to about 60 weight % of dinitroketone, wherein reacting the nitromalondialdehyde with the dinitroketone produces a mixture, wherein the mixture is subjected to cyclohydrative mechanism to remove excess $H_2O$ to produce environmentally friendly picric acid explosive. In embodiments of the present invention the dinitroketone comprises about 56 weight % and the nitromalondialdehyde comprises about 44 weight %. In other embodiments, the dinitroketone comprises at least one of 1,3-dinitroacetone or nitroacetone.

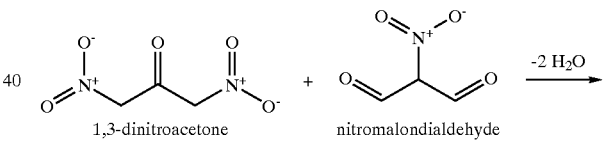

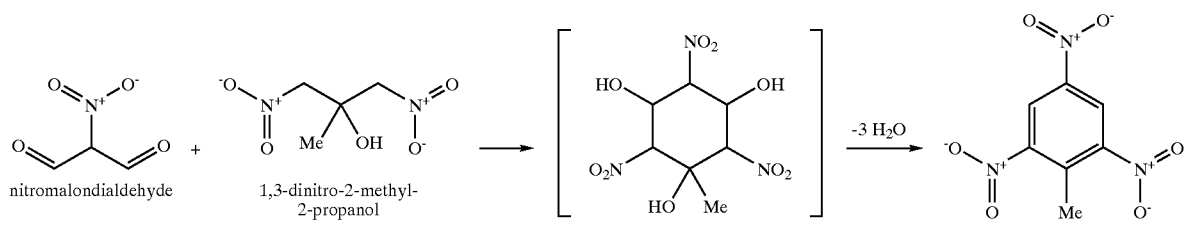

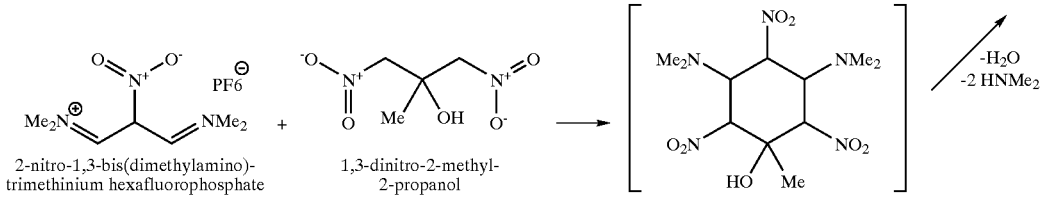

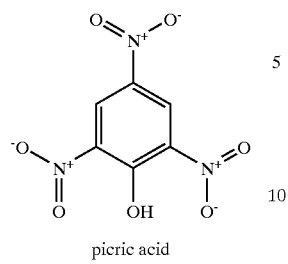

picric acid

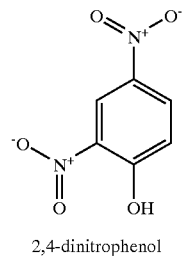

2,4-dinitrophenol

Another embodiment of the present invention includes a method for making environmentally friendly 2,4-dinitrophenyl compound comprising, providing a nitromalondialdehyde, providing a nitroacetone, reacting the nitromalondialdehydes with the nitroacetone to produce a mixture, and subjecting the mixture to a cyclodehydrative mechanism to produce environmentally friendly 2,4-dinitrophenyl compound.

Embodiments of the present invention include the nitromalondialdehydes comprising about 50 to about 55 weight % and the nitroacetone comprising about 45 to about 50 weight %. In other embodiments, the nitromalondialdehydes comprises about 53 weight % and the nitroacetone comprises about 47 weight %. Other embodiments include the nitroacetone comprising at least one of 1-nitroacetone. The method includes the cyclodehydrative mechanism subjecting the mixture to dehydration to remove excess H$_2$O.

Embodiments of the present invention include the 2,4-dinitrophenyl compound produced by this environmentally friendly method. Another embodiment includes an environmentally friendly 2,4-dinitrophenyl compound comprising about 50 to about 55 weight % of nitromalondialdehyde and about 45 to about 50 weight % of nitroacetone, wherein reacting the nitromalondialdehyde with the nitroacetone produces a mixture, wherein the mixture is subjected to cyclohydrative mechanism to remove excess H$_2$O to produce environmentally friendly 2,4-dinitrophenyl. In other embodiments, the 2,4-dinitrophenyl compound comprises about 53 weight % of nitromalondialdehyde and about 47 weight % of nitroacetone.

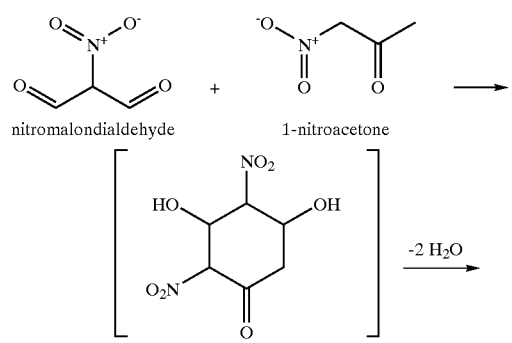

Experimental Results

The following experimental results led to the development of environmentally friendly methods for making 2,4,6-trinitrotoluene (TNT) compounds, picric acid explosives, and 2,4-dinitrophenyl compounds by utilizing cyclodehydrative condensation mechanisms. These methods for the synthesis of TNT will not have a 'red water' waste stream. In one embodiment of the present invention, the synthesis will provide the desired tri-nitro isomer of TNT as the only product, thereby eliminating the need for sellite washing.

The present invention was formulated after reviewing a report by Hill and Torrey on the self-condensation of nitromalonaldehyde that gave 2,4,6-trinitrobenzene (TNB) albeit in modest yield of ~20%.

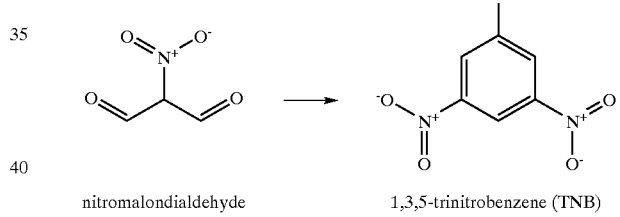

nitromalondialdehyde    1,3,5-trinitrobenzene (TNB)

This reaction was repeated in these experiments on one occasion and the isolated yield was ~16%, the product had nuclear magnetic resonance (NMR) spectra identical to authentic samples of TNB. This style of cyclodehydrative condensation is also represented by the synthesis of 1,3,5-triacetylbenzene from formylacetone.

The cyclodehydration process described by the present invention was demonstrated using nitroacetone and nitromalonaldehyde under basic conditions yields the aromatized product, 2,4-dinitrophenyl. The material is spectroscopically identical to a commercially available product. It was therefore envisioned that nitromalonaldehyde or β-nitrovinamidinium PF$_6$ salt and 1,3-dinitro-2-methyl-2-propanol would react in the cyclodehydrative manner to furnish TNT. The use of β-nitrovinamidinium PF$_6$ salts in cyclodehydration reactions was shown with acetone and other ketones. Because of the reactivity of nitroacetone, it is also envisioned that 1,3-dinitroacetone will react with nitromalonaldehyde in the cyclodehydrative mechanism to form the explosive picric acid. The use of alternative dinitroalkanes was believed to lead to TNT as well, such as trans-1,3-dinitro-2-methyl-1-propene. This compound will cyclodehydrate in the presence of nitromalonaldehyde or β-nitrovinamidinium $PF_6$ salt to form TNT.

2,4-Dinitro-1-hydroxybenzene

A 50 mL round bottom flask was charged with 2 parts sodium nitromalonaldehyde monohydrate followed by 20 parts distilled $H_2O$. After the salt has completely dissolved, 1.18 parts 1-nitro-2-propanone was added to the reaction followed by a solution of 1 part sodium hydroxide in 2 parts distilled $H_2O$. The mixture is stirred for 18 hr at room temperature. After this time, 3.15 parts concentrated HCl was added to the reaction causing an immediate color change. The reaction mixture was extracted several times with $CHCl_3$. The extracts were collected, dried over anhydrous $MgSO_4$ and evaporated. The remaining residue was column chromatographed ($SiO_2$; $CH_2Cl_2$) to obtain the title compound as a pale yellow solid weighing 440 mg. $^1H$ NMR ($CDCl_3$, 200 MHz) δ 11.04 (s, OH), 9.09 (d, J=2.8 Hz, H-3), 8.48 (dd, J=2.8 and 8.8 Hz, H-5), 7.35 (d, J=9.4 Hz, H-6); the NMR spectra is identical to the commercially available product.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for making 2,4-dinitrophenyl compound comprising:
   providing a nitromalondialdehyde;
   providing a nitroacetone;
   reacting said nitromalondialdehyde with said nitroacetone to produce a mixture; and
   subjecting said mixture to a cyclodehydrative mechanism to produce environmentally friendly 2,4-dinitrophenyl compound.

2. The method according to claim 1, wherein said nitromalondialdehyde comprises about 50 to about 55 weight % and said nitroacetone comprises about 45 to about 50 weight %.

3. The method according to claim 1, wherein said nitromalondialdehyde comprises about 53 weight % and said nitroacetone comprises about 47 weight %.

4. The method according to claim 1, wherein said cyclodehydrative mechanism includes subjecting said mixture to dehydration to remove excess $H_2O$.

* * * * *